(12) United States Patent
Ryu et al.

(10) Patent No.: US 7,373,196 B2
(45) Date of Patent: May 13, 2008

(54) PHYSIOLOGICAL SIGNAL DETECTION MODULE, MULTI-CHANNEL CONNECTOR MODULE AND PHYSIOLOGICAL SIGNAL DETECTION APPARATUS USING THE SAME

(75) Inventors: Chang Yong Ryu, Daejeon (KR); Seung Hwan Kim, Daejeon (KR); Youn Tae Kim, Daejeon (KR)

(73) Assignee: Electronics and Telecommunications Research Institute, Daejon (KR)

( * ) Notice: Subject to any disclaimer, the term of this patent is extended or adjusted under 35 U.S.C. 154(b) by 416 days.

(21) Appl. No.: 11/027,162

(22) Filed: Dec. 29, 2004

(65) Prior Publication Data

US 2005/0283061 A1 Dec. 22, 2005

(30) Foreign Application Priority Data

Jun. 22, 2004 (KR) ...................... 10-2004-0046613

(51) Int. Cl.
*A61B 5/04* (2006.01)
(52) U.S. Cl. ...................................... 600/372
(58) Field of Classification Search ................. 600/372
See application file for complete search history.

(56) References Cited

U.S. PATENT DOCUMENTS

| | | | | |
|---|---|---|---|---|
| 3,500,823 A | * | 3/1970 | Richardson et al. | ......... 600/372 |
| 3,620,208 A | * | 11/1971 | Higley et al. | ................ 600/395 |
| 4,432,365 A | * | 2/1984 | Leist | .......................... 600/358 |
| 4,763,659 A | | 8/1988 | Dunseath, Jr. | |
| 4,865,039 A | | 9/1989 | Dunseath, Jr. | |
| 5,197,471 A | | 3/1993 | Otero | |
| 5,224,479 A | | 7/1993 | Sekine | |
| 6,067,464 A | | 5/2000 | Musha | |
| 6,138,044 A | * | 10/2000 | Svedman | ..................... 600/387 |
| 6,253,099 B1 | * | 6/2001 | Oskin et al. | ................ 600/372 |
| 6,408,200 B1 | | 6/2002 | Takashina | |
| 6,445,940 B1 | | 9/2002 | Gevins et al. | |
| 2005/0177038 A1 | * | 8/2005 | Kolpin et al. | ............... 600/372 |

FOREIGN PATENT DOCUMENTS

| | | |
|---|---|---|
| JP | 07-163528 | 6/1995 |
| JP | 11299751 | 11/1999 |
| JP | 2001178753 | 7/2001 |
| KR | 10-2004-0062607 | 7/2004 |

OTHER PUBLICATIONS

"Reduction of Skin Impedance By the Improvement of the Blood Circulation", J. Bau, et al., 2001 IEEE, 2001 Proceedings of the 23rd Annual EMBS Intl Conf. Oct. 25-28, pp. 3081-3082.
"The Mosaic Electrical Characteristics of the Skin", D. Panescu, et al., 1993 IEEE, IEEE Transactions on Biomedical Engineering, vol. 40, No. 5, May 1993, pp. 434-439.

* cited by examiner

*Primary Examiner*—Lee S. Cohen
(74) *Attorney, Agent, or Firm*—Blakely, Sokoloff, Taylor & Zafman LLP

(57) ABSTRACT

Provided is a physiological signal detection module which has a heating member and a multi-channel connector. The heating member maintains an electrode's contact with a user skin at a constant temperature, and the multi-channel connector module for electrical connection transmits the physiological signal to an external physiological signal detection apparatus. It is possible to prevent the skin from being directly contacted with the electrode in the cold state and have a less impact given by a change of the impedance due to a skin temperature based on the change of the season and external temperature, so that the stable physiological signal can be detected without distortion.

6 Claims, 5 Drawing Sheets

PHYSIOLOGICAL SIGNAL DETECTION MODULE, MULTI-CHANNEL CONNECTOR MODULE AND PHYSIOLOGICAL SIGNAL DETECTION APPARATUS USING THE SAME

CROSS-REFERENCE TO RELATED APPLICATION

This application claims priority to and the benefit of Korean Patent Application No. 2004-46613, filed on Jun. 22, 2004, the disclosure of which is incorporated herein by reference in its entirety.

BACKGROUND

1. Field of the Invention

The present invention relates to a physiological signal detection module, a multi-channel connector module and a physiological signal detection apparatus using the same, capable of detecting a stable physiological signal without distortion. The physiological signal detection module has a heating member and a multi-channel connector. The heating member maintains an electrode's contact with a user skin at a constant temperature, and the multi-channel connector module for electrical connection transmits the physiological signal, which is detected from the electrode, to an external physiological signal detection apparatus.

2. Discussion of Related Art

In general, an electrode is attached to a user skin of a subject to measure a physiological signal. A typical electrode is a disposable electrode, e.g., a wet electrode. To reduce impedance between the user skin and the electrode, a conductive gel is applied to the metallic electrode, thereby facilitating converting ion current flowing in a living body into an electric current.

However, the disposable electrode using the conductive gel incurs a skin trouble such as a reddish skin and stinging pain, when used for a long-time measurement. Therefore, it is somewhat difficult to use the disposable electrode in the portable physiological detection apparatus that monitors the physiological signals for a long-time.

Accordingly, there has been proposed a method of using a dry electrode rather than the conductive gel, which is suitable to measure the physiological signal for a relatively long time. The dry electrode uses a conductive polymer or metal having good conductivity. However, there are problems in that the physiological signal is distorted due to difference of impedance between the user skin and the dry electrode, and it is possible to get the stable physiological signal only after a predetermined time elapses from when the dry electrode is attached to the user skin.

To solve the afore-mentioned problems, a method of placing a buffer as close as possible to the dry electrode to match the impedance was proposed. Conventionally, the buffer is placed at a connector portion of the dry electrode, and a power is connected to the physiological signal detection apparatus using an independent cable. This is referred to as an active electrode. However, the active electrode has problems in that its connector should be designed such that the power can be supplied from the physiological signal detection apparatus to the active electrode through the connector.

To solve the afore-mentioned problems, several technologies have been proposed. For instance, U.S. Pat. No. 4,865,039 entitled to "Dry electrode system for detection of biopotentials and dry electrode making electrical and mechanical connection to a living body" discloses a system in which the connector includes a circuit for amplifying physiological signals and a battery pack for supplying power to an amplification circuit is mounted to the connector connected with the measurement apparatus.

However, in the foregoing conventional technology, the battery pack for supplying power is required for each of the dry electrodes, so that the multi-channel system becomes complicated and expensive.

SUMMARY OF THE INVENTION

The present invention is directed to a physiological signal detection module comprising an electrode housing to which an electrode contacting a user skin is detachably connected and which has a printed circuit board (PCB) mounted with various circuits for matching impedance between the electrode and the user skin; and a heating member interposed between the electrode and the electrode housing to increase the temperature of the electrode to a certain degree.

The present invention is also directed to a multi-channel connector module that connects the physiological signals, detected from the electrode that is in contact with the user skin, into one body to transmit to an external physiological signal detection apparatus and having a power supply unit for supplying power to detect various physiological signals.

One aspect of the present invention is to provide a physiological signal detection module including: an electrode in contact with a user skin to detect various physiological signals; an electrode housing detachably connected to the electrode and having a printed circuit board (PCB) mounted with various circuit for matching impedance between the skin and the electrode; and a heating member interposed between the electrode and the electrode housing, and being supplied with an external power to increase the temperature of the electrode to a certain degree.

Another aspect of the present invention is to provide a multi-channel connector module including: a connector housing that forms a whole body; a plurality of connectors for electrical connection to transmit various physiological signals to an external physiological detection apparatus, wherein a portion of the connector is exposed on one side of the connector housing; and a power supply unit for supplying power to the external physiological signal detection module, wherein the power supply unit is arranged inside the connector housing and electrically connected to the connector to detect the various physiological signals.

BRIEF DESCRIPTION OF THE DRAWINGS

The above and other features of the present invention will be described in reference to certain exemplary embodiments thereof with reference to the attached drawings in which.

DETAILED DESCRIPTION OF THE INVENTION

Exemplary embodiments of the present invention will now be described more fully with reference to the accompanying drawings. This invention may, however, be embodied in different forms and should not be construed as limited to the embodiments set forth herein. Rather, these embodiments are provided so that this disclosure will be thorough and complete, and will fully convey the scope of the invention to those skilled in the art.

Figure 1:
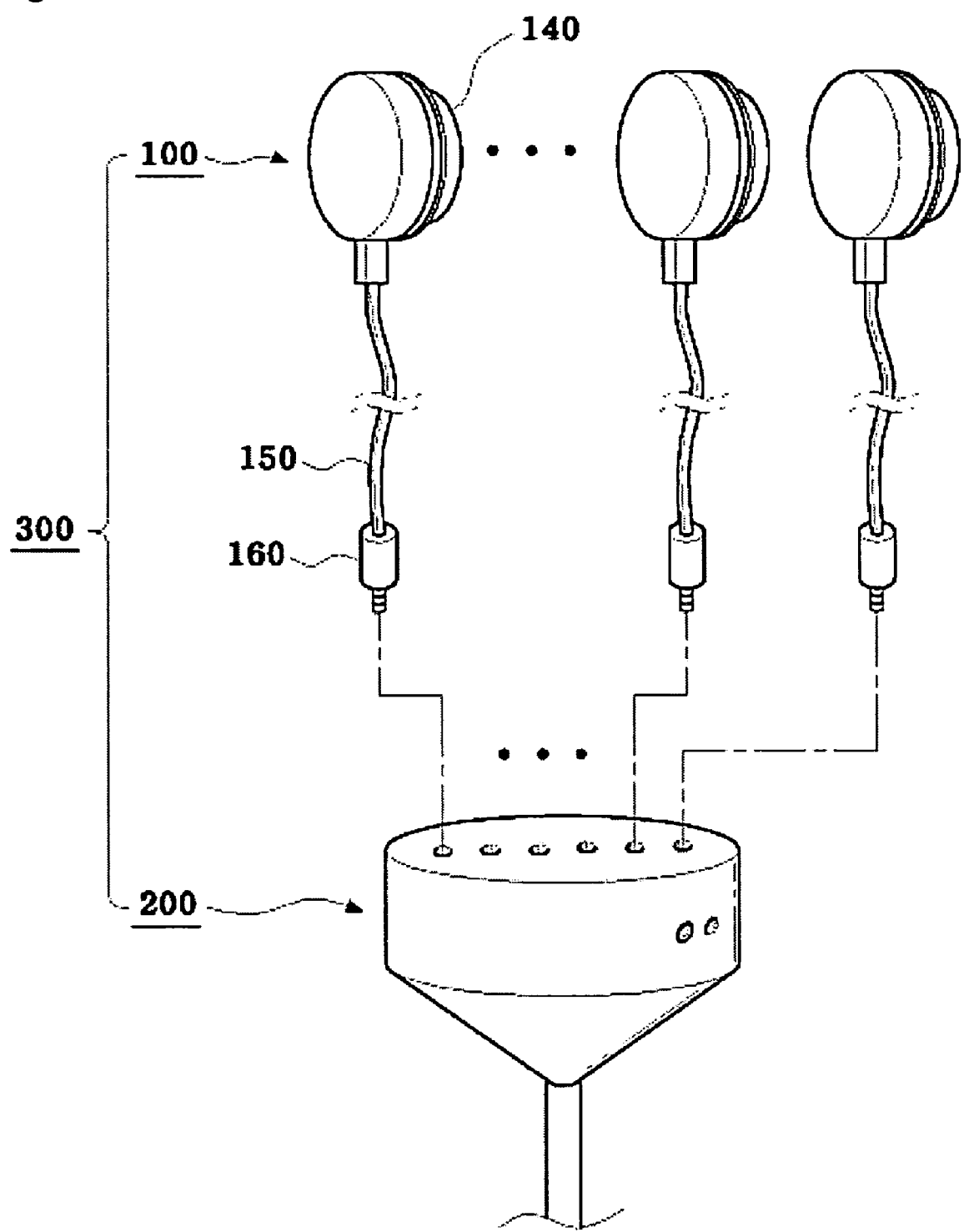
FIG. 1 is a perspective view for explaining a physiological signal detection apparatus including a physiological signal detection module and a multi-channel connector module according to an embodiment of the present invention.

FIG. 1 is a perspective view for explaining a physiological signal detection apparatus including a physiological signal detection module and a multi-channel connector module according to an embodiment of the present invention;

Referring to FIG. 1., a physiological signal detection apparatus 300 according to an embodiment of the present invention includes a plurality of physiological signal detection modules for detecting electrocardiogram (ECG), electrodermal activity (EDA), body fat, and respiration via electrodes 140 contacting with a user skin. Further, the physiological signal detection apparatus 300 includes a multi-channel connector module 200 for electrical connection to transmit various physiological signals detected from a plurality of the electrodes 140 to an external physiological signal detection apparatus 400 (in FIG. 6). The plurality of physiological detection modules 100 and the multi-channel connector module 200 can be electrically and detachably connected.

Here, it is desirable that the physiological signal detection modules 100 and the multi-channel connector module 200 be electrically and detachably connected to a connector 210 of the multi-channel connector module 200 using connection jacks 160. The connection jacks 160 are arranged at ends of the cables 150.

Figure 2:
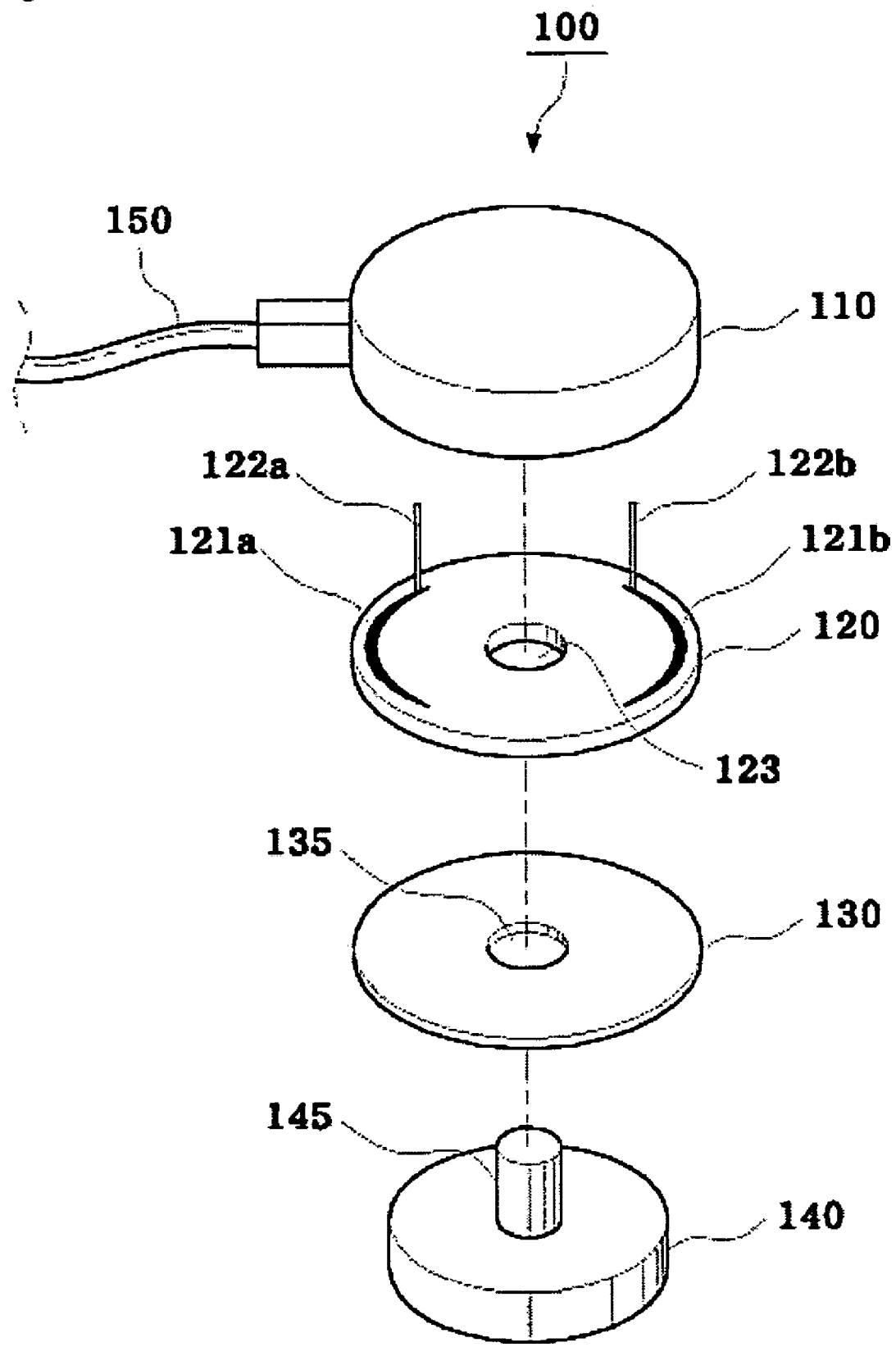
FIG. 2 is a disassembled perspective view for specifically explaining a physiological signal detection module according to an embodiment of the present invention in more detail.
Figure 3:
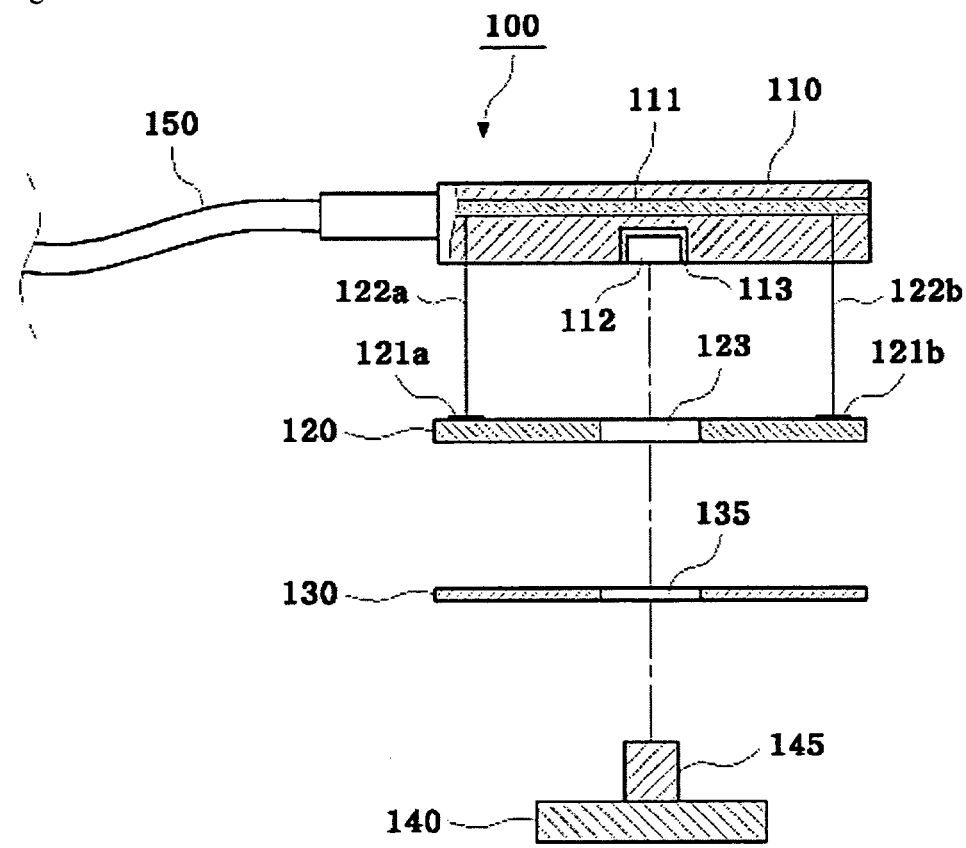
FIG. 3 is a vertical cross sectional view of FIG. 2.

FIG. 2 is a disassembled perspective view for specifically explaining a physiological signal detection module, and FIG. 3 is a vertical cross sectional view of FIG. 2.

Referring to FIGS. 2 and 3, the physiological signal detection module includes an electrode housing 110, a heating member 120, an insulating member 130 and an electrode 140.

Here, the electrode housing 110 is provided as a whole body in a flat circular pattern, and a printed circuit board mounted with various circuits (e.g., buffer and amplification circuit, etc.) for matching impedance between the electrode 140 and the skin is arranged inside the electrode housing 110. At the center of the bottom of the electrode housing 110, a circular coupling groove 112 is formed, and a fixing cap 113 is fixedly connected to cover all over the coupling groove 112.

Here, the fixing cap 113 has the same pattern as the coupling groove 112, and is preferably made of metal having good conductivity (e.g., Cu, Ag, Pt) such that the coupling protrusion unit 145 of the electrode 140 is fixedly connected to transmit various physiological signals detected from the electrode 140 to the outside.

In addition, one side of the electrode housing 110 is electrically connected to the printed circuit board 111, and the end of the electrode housing 110 is connected to a cable 150 of the predetermined length having a connection jack 160 (in FIG. 1).

The electrode is formed in a flat circular pattern, and on top of it, the circular coupling protrusion unit 145 are protruded in one body to be fixedly inserted into the fixing cap 113 of the electrode housing 110.

In addition, the electrode 140, which is fixedly connected to the bottom of the electrode housing 110 and detects various physiological signals by directly contacting with the user skin, is preferable made of a dry electrode formed with metal having good conductivity (e.g., Ti, Au, Pt and Ag/AgCl).

Further, the heating member 120 is arranged between the electrode housing 110 and the electrode 140, and heats the electrode 140 up to a certain temperature (e.g., about 34 to 36.5° C). According as the electrode 140 is heated by the heating member 120, the electrode 140 in a cold state is prevented from being directly contacted with the user skin, and the physiological signals become more stable than those from the conventional electrode.

The heating member 120 is made of a two-dimensional (e.g, a circular plane or film) resistor, and a (+) power connection electrode 112a and a ground power connection electrode 121b are electrically connected to both planes, respectively, to generate a uniform heat. A (+) power connection line 122a and a ground power connection line 122b are electrically connected to ends of the (+) power connection electrode 112a and the ground power connection electrode 121b, respectively, to receive external power via the printed circuit board 111. At the center of the heating member 120, an opening is formed through which the coupling protrusion unit 145 is penetrated. In addition, the diameter of the opening 123 is formed larger than that of the coupling protrusion unit 145 so as not to contact with the coupling protrusion unit 145 of the electrode 140.

While the exemplary embodiment of the present invention is described with reference to the two-dimensional resistor, the present invention is not limited hereto, and there may be provided with a typical one-dimensional resistor.

In addition, an insulating member 130 is further arranged between the heating member 120 and the electrode 140 to prevent a current flowing into the heating member 120 from flowing into the user skin via the electrode 140.

The insulating member 130 is made of an insulating paper in a flat circular pattern. At the center of the insulating member 130, an opening 135 is formed through which the coupling protrusion unit 145 of the electrode 140 is penetrated. It is desirable that the diameter of the opening 135 is formed larger than that of the coupling protrusion unit 145 so as not to contact with the coupling protrusion unit 145 of the electrode 140.

While the insulating member 130 applied to the embodiment of the present invention is preferably made of the thin insulating paper, the present invention is not limited hereto and an insulating such as plastic, rubber, glass and lumber may also be used.

Figure 4:
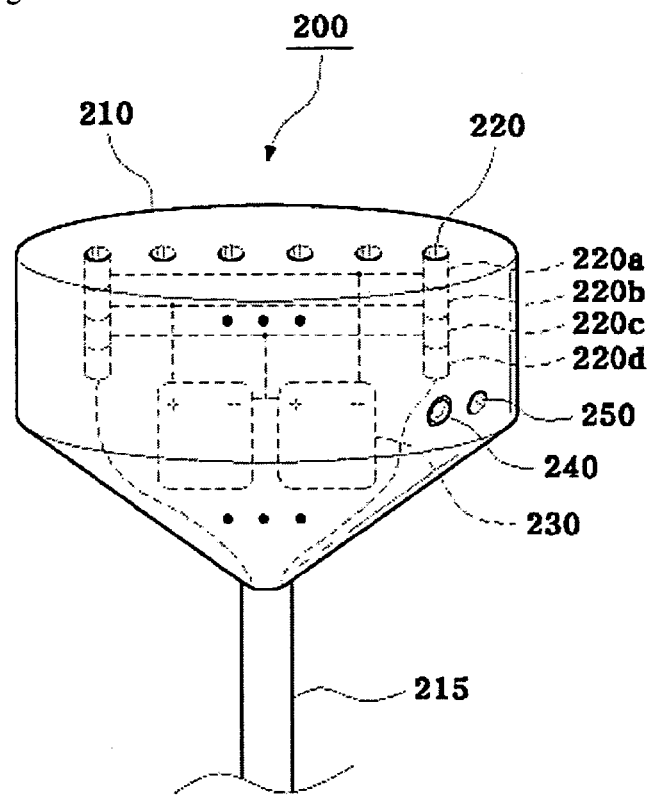
FIG. 4 is a perspective view for specifically explaining a multi-channel connector module according to an embodiment of the present invention.

FIG. 4 is a perspective view for specifically explaining a multi-channel connector module according to an embodiment of the present invention.

Referring to FIG. 4, the multi-channel connector module 200 according to an embodiment of the present invention includes a connector housing 210, a plurality of connectors 220 and a power supply unit 230.

Here, the connector housing 210 is provided as a whole body in a flat elliptical funnel-like shape. A cable 215 having a predetermined length and electrically connected to an external physiological signal detection apparatus 400 (in FIG. 6) is connected to the bottom of the connector housing 210.

A plurality of connectors 220, provided inside the connector housing 210 and used to electrically connect with the connection jack 160 (in FIG. 1), are arranged at a constant interval such that a portion of the connector is exposed on the top of the connector housing 210.

In addition, the connector 220 is split by an insulating material into 4 parts, i.e., a (−) power connection unit 220a, a (+) power connection unit 220b, a ground power connection unit 220c and a signal connection unit 220d.

The power supply unit 230 electrically connected to the connector 220 is arranged inside the connector housing 210, serving to supply power to the physiological signal detection modules 100 (in FIG. 1) so that various physiological signals can be detected.

The power supply unit may be a secondary battery, which is, for example, a rechargeable battery, so that additional protection circuit is not required. In addition, the power supply unit is preferably implemented with a plurality of Li-polymer batteries connected in series, which can be fabricated in a thin film and used for a long time in a small volume and light weight without memory effect.

In addition, the (+) power of the power supply unit 230 is connected to the (+) power connection unit 220b of the connector 220, and the (−) power of the power supply unit 230 is connected to the (−) power connection unit 220a, respectively. Further, a series connection is electrically connected to the ground power connection unit 220c of the connector 220.

Further, one side of the connector housing has a state display unit (e.g., LED) 240 for checking charging state of the battery and a power supply connector 250 for connecting the battery to the external power to supplement power shortage of the battery.

Further, according to an embodiment of the present invention there exist 6 channels, i.e., 6 electrodes 140, where the cable 215 connected to the external physiological signal detection apparatus 400 (in FIG. 6) includes 6 signal lines and one ground line.

Figure 5:
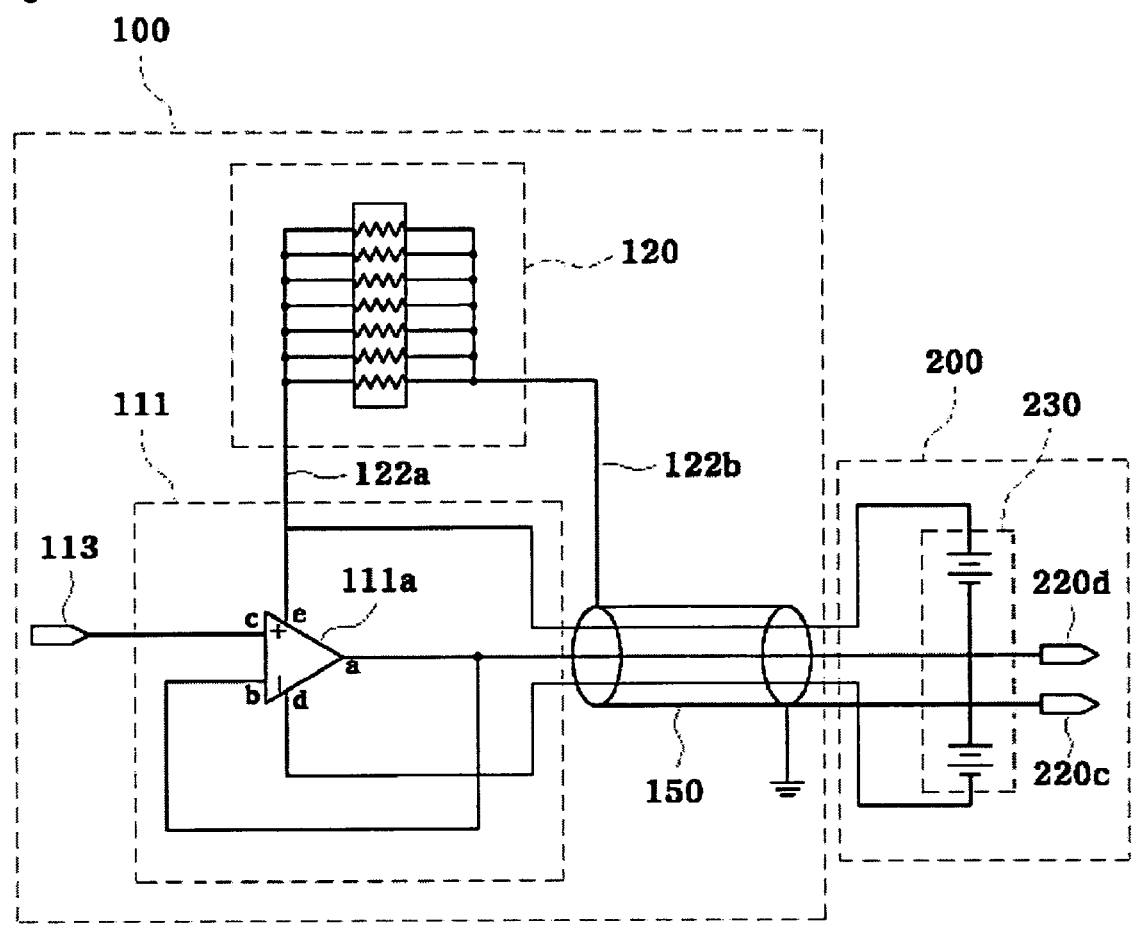
FIG. 5 is a circuit diagram for explaining a physiological signal detection apparatus including a physiological signal detection module and a multi-channel connector module according to an embodiment of the present invention.

FIG. 5 is a circuit diagram for explaining a physiological signal detection apparatus including a physiological signal detection module and a multi-channel connector module according to an embodiment of the present invention.

Referring to FIG. 5, an electrode 140 (in FIG. 2) and an OP-AMP 111a for matching the impedance of skin are mounted on a printed circuit board 111 of the physiological signal detection module 100.

For the OP-AMP 111a, a non-inverting input terminal c is connected to a fixing cap 113 of the electrode housing 110 (in FIG. 2), and an inverting input terminal b is connected to an output terminal a, and the output terminal a is further connected to the signal connection unit 220d of the connector 220 (in FIG. 4) via the cable 150.

In addition, the (+) power supply of the battery constituting the power supply unit 230 is connected to the (+) power connection unit 220b (in FIG. 4) of the connector 220, so that it is connected to the power supply terminal e of the OP-AMP 111a and the one end of the heating member 120, i.e., the (+) power supply connection electrode 121a (in FIG. 3) and the (+) power supply connection line 122a, via the cable 150. Further, the (−) power supply of the battery is connected to the (−) power supply connection unit 220a of the connector 220 (in FIG. 4) so that it is connected to the reference terminal d of the OP-AMP 111a via the cable 150.

Further, the other end of the heating member 120, i.e., the ground power connection electrode 121b (in FIG. 3) and the ground power connection line 122b are grounded to the ground power connection unit 220c (in FIG. 4) of the connector 220 via the cable 150. Here, the cable 150 can use a ground line as a shielding wire.

According to a physiological signal detection apparatus including the physiological signal detection module 100 and a multi-channel connector module 200 of the present invention described above, a variety of physiological signals detected from the electrodes 140 are transmitted to the non-inverting input terminal c of the OP-AMP 111a via the coupling protrusion unit 145 (in FIG. 2) and the fixing cap 113. The physiological signals outputted through the OP-AMP 111a are transmitted to the multi-channel connector module 200 via the cable 150 and provided to the external physiological signal detection apparatus 400 (in FIG. 6). Further, the OP-AMP 111a and the heating member 120 receive power form the power supply unit 230 of the multi-channel connector module 200.

Figure 6:
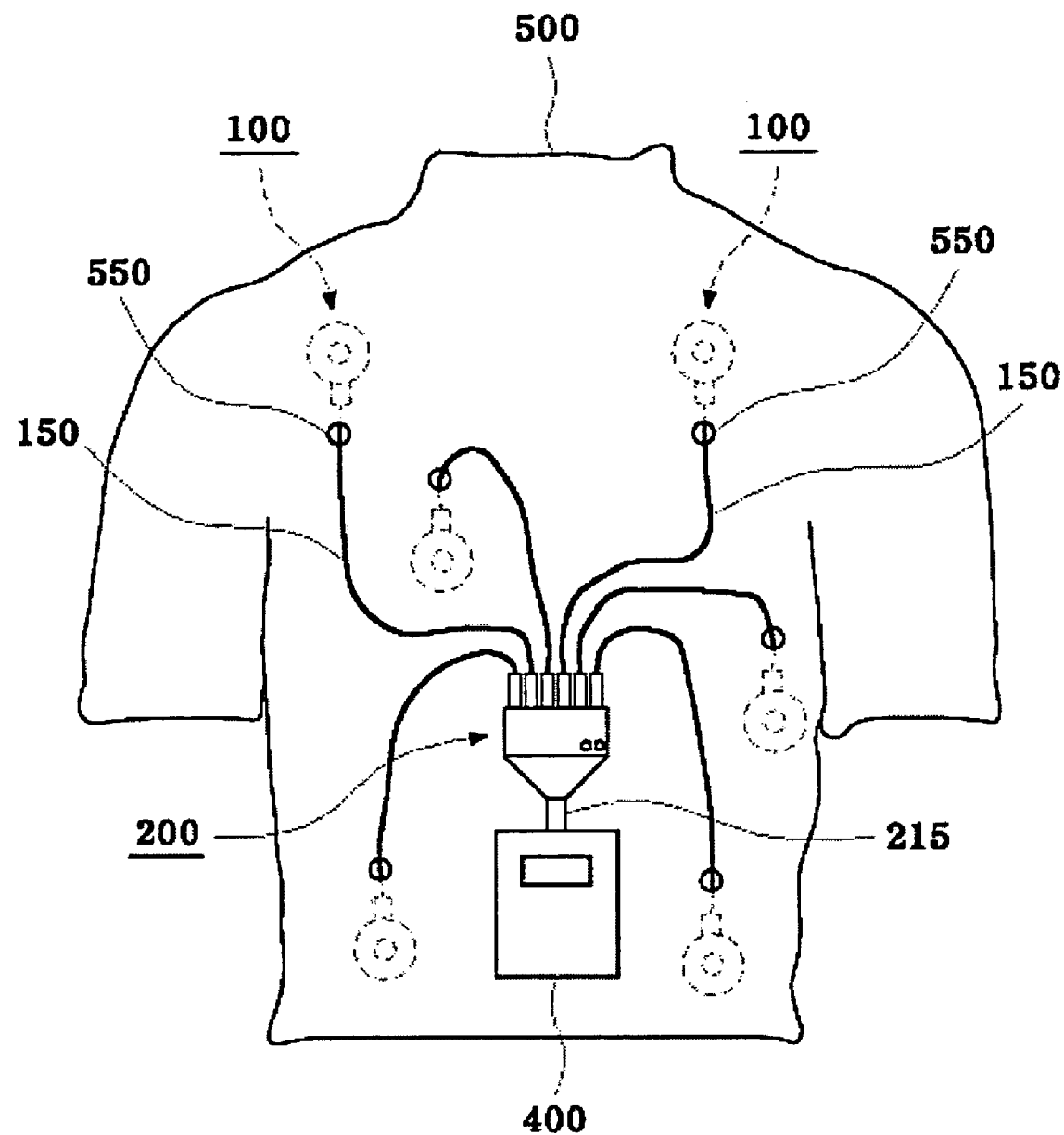
FIG. 6 is a diagram illustrating an exemplary arrangement of a physiological signal detection apparatus including a physiological signal detection module and a multi-channel connector module according to an embodiment of the present invention.

FIG. 6 is a diagram illustrating an exemplary arrangement of a physiological signal detection apparatus including a physiological signal detection module and a multi-channel connector module according to an embodiment of the present invention.

Referring to FIG. 6, a plurality of physiological signal detection modules 100 are attached to the proper positions on the shirts-type clothing 500 to make the electrodes 140 contact with the skin, and the cables 150 are stretched out of the physiological signal detection modules 100 to clothing 500 through a plurality of penetration holes 550 to be connected to the multi-channel connector module 200. Here, to make the cables 150 unnoticeable, a portion of clothing 500 can be supplied in double covers so that the cables 150 can be located between the inner cover and the outer cover.

In addition, the cable 215 of the multi-channel connector module 200 is electrically connected to the physiological signal detection apparatus 400 inserted into, for example, pockets (not shown) provided at the proper positions of the clothing 500.

Further, the physiological signal detection apparatus 400 performs amplification, processing, storage and transmission of various physiological signals detected from respective physiological signal detection modules 100. The physiological signal can be transmitted to the computer using a serial communication, or a real-time wireless transmission such as a Bluetooth, ZigBee or the like. Alternatively, the physiological signal can be transmitted to a remote place via an apparatus using a cellular phone module, for example, a personal digital assistant (PDA).

While, in the physiological signal detection module 100 applied to the present invention, the electrode housing 110, the heating member 120, the insulating member 130 and the electrode 140 are provided in a flat circular shape, the present invention is not limited hereto and various shapes such as triangle, rectangular, and polygons may be provided herein.

As illustrated above, the present invention provides a physiological signal detection module, a multi-channel connector module and a physiological signal detection apparatus using the same, capable of detecting a stable physiological signal without distortion. Through the present invention, it is possible to prevent the skin from directly contacting with the electrode in a cold state and to have a less impact given by change of the impedance due to a skin temperature based on the change of the season and external temperature. Thus, the stable physiological signals can be detected without distortion.

In addition, a commonly used snap-type disposable electrode as well as a dry electrode can be used in the present invention, and the general-purpose physiological signal detection apparatus can be simply connected. Thus, there are no additional required costs.

While the exemplary embodiments of the present invention directed to the physiological signal detection module, the multi-channel connector module and the physiological signal detection apparatus using the same have been described with reference to the detailed description and the attached drawings, these embodiments are illustrative only, but not for limiting the scope of the present invention claimed in the following claims. Therefore, those skilled in the art will appreciate that a variety of modifications and the equivalents thereof can be made. Thus, the scope of the present invention should be defined by the appended claims.

What is claimed is:

1. A physiological signal detection module comprising:
   an electrode adapted to be in contact with a user skin to detect various physiological signals;
   an electrode housing detachably connected to the electrode and having a printed circuit board (PCB) mounted with an operational amplifier for matching impedance of the skin with the electrode; and
   a heating member coupled to the operational amplifier and interposed between the electrode and the electrode housing, and being supplied with an external power to increase the temperature of the electrode to a certain degree.

2. The physiological signal detection module according to claim 1, wherein the electrode is a dry electrode made of metal having a good conductivity.

3. The physiological signal detection module according to claim 1, wherein the heating member is any one of a one-dimensional resistor, a two-dimensional plane-type resistor, and a two-dimensional film-type resistor.

4. The physiological signal detection module according to claim 1, further comprising an insulating member interposed between the electrode and the heating member to prevent a current flowing into the heating member from flowing into the user skin through the electrode.

5. The physiological signal detection module according to claim 1, wherein the heating member adjusts the temperature of the electrode in a range between 34° C. to 36.5° C.

6. The physiological signal detection module according to claim 5, wherein the heating member adjusts the temperature of the electrode is based on a change of skin impedance due to external temperature.

* * * * *